(12) United States Patent
Almås

(10) Patent No.: US 10,675,299 B2
(45) Date of Patent: *Jun. 9, 2020

(54) HAND DISINFECTANT

(71) Applicant: WIAB Water Innovation AB, Malmo (SE)

(72) Inventor: Geir Hermod Almås, Oslo (NO)

(73) Assignee: WIAB WATER INNOVATION AB, Malmo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,076

(22) Filed: May 27, 2016

(65) Prior Publication Data
US 2016/0271171 A1 Sep. 22, 2016

Related U.S. Application Data

(63) Continuation-in-part of application No. 14/618,820, filed on Feb. 10, 2015, which is a continuation-in-part of application No. 13/770,738, filed on Feb. 19, 2013, now Pat. No. 9,492,479, application No. 15/167,076, filed on May 27, 2016, which is a continuation of application No. 14/618,799, filed on Feb. 10, 2015, which is a continuation of application No. 13/770,738, filed on Feb. 19, 2013, now Pat. No. 9,492,479.

(60) Provisional application No. 61/600,344, filed on Feb. 17, 2012.

(51) Int. Cl.
*A61K 33/20* (2006.01)
*A61K 31/19* (2006.01)
*A61K 9/00* (2006.01)
*C01B 11/04* (2006.01)

(52) U.S. Cl.
CPC ............ *A61K 33/20* (2013.01); *A61K 9/0014* (2013.01); *A61K 31/19* (2013.01); *C01B 11/04* (2013.01)

(58) Field of Classification Search
CPC ... A61K 49/0021; A61K 9/0048; A61K 47/06
See application file for complete search history.

(56) References Cited

U.S. PATENT DOCUMENTS

| | | | |
|---|---|---|---|
| 2,438,781 A | 3/1948 | Kamlet | |
| 4,017,592 A | 4/1977 | Penard et al. | |
| 4,983,634 A | 1/1991 | Corby | |
| 5,152,915 A | 10/1992 | Ralston, Jr. et al. | |
| 5,456,211 A | 10/1995 | Stevenson | |
| 6,333,054 B1 | 12/2001 | Rogozinski | |
| 6,564,508 B1 | 5/2003 | Buchan | |
| 6,627,207 B1 * | 9/2003 | Petersen | A01N 25/04 424/401 |
| 8,784,900 B2 * | 7/2014 | Northey | A61K 33/00 252/181.4 |
| 2008/0008621 A1 * | 1/2008 | Ikeda | A01N 59/00 422/37 |
| 2009/0258083 A1 | 10/2009 | Calderon | |
| 2012/0148516 A1 | 6/2012 | Abel et al. | |
| 2015/0150906 A1 | 6/2015 | Hinderson et al. | |
| 2015/0150907 A1 | 6/2015 | Hinderson et al. | |
| 2016/0271171 A1 | 9/2016 | Almas | |
| 2017/0266227 A1 | 9/2017 | Almas | |

FOREIGN PATENT DOCUMENTS

| | | |
|---|---|---|
| EP | 1829449 A1 | 9/2007 |
| JP | H10309582 A | 11/1998 |
| JP | 2003040716 A | 2/2003 |
| JP | 2007-326050 A | 12/2007 |
| JP | 2011056377 A | 3/2011 |
| JP | 2011-229833 A | 11/2011 |
| WO | 94/21125 A1 | 9/1994 |
| WO | 2001028336 A1 | 4/2001 |
| WO | 2005065383 A2 | 7/2005 |
| WO | 2013121294 A1 | 8/2013 |
| WO | 2017203364 A1 | 11/2017 |

OTHER PUBLICATIONS

International Search Report and Written Opinion dated Jul. 30, 2013, for International Application No. PCT/IB2013/000682, filed Feb. 19, 2013 (7 pages).

Kuroiwa, K., et al., "Augmenting effect of acetic acid for acidification on bactericidal activity of hypochlorite solution", Lett. Applied Microbiol., 2003, pp. 46-49.

Wang, L., et al., "Hypoohlorous Acid as a Potential Wound Care Agent", J. Burns Wounds, 2007, pp. 65-79.

Dash, Sukalyan et al. "Oxidation by Permanganate: Synthetic and Mechanistic Aspects," Tetrahedron, vol. 65, 2009, pp. 707-739 (33 Pages).

Boddie, R.L. et al., "Efficacy of Teat Dips Containing a Hypochlorous Acid Germicide Against Experimental Challenge with *Staphylococcus aureus* and *Streptococcus agalactiae*", J. Dairy Sci., 1996, pp. 1683-1688 (6 Pages).

Schmittinger, P. et al. "Chlorine", Wiley, 2000, pp. 160-164 (7 Pages).

(Continued)

*Primary Examiner* — Robert S Cabral
(74) *Attorney, Agent, or Firm* — Brown Rudnick LLP; Thomas C. Meyers

(57) ABSTRACT

The invention provides a skin disinfectant for treating skin with eczema, preventing bacterial proliferation, and removing biofilm. Compositions of the invention include hypochlorous acid, acetic acid, water, and one or more additives or excipients. The formulation process removes metal ions, reduces ionic strength, controls pH, and reduces exposure to air, thus improving stability and lengthening shelf-life.

19 Claims, 6 Drawing Sheets

(56) References Cited

OTHER PUBLICATIONS

Plaizier-Vercammen, Jacqueline, "Rheological Properties of Laponite XLG, A Synthetic Purified Hectorite", Die Pharmazie: An International Journal of Pharmaceutical Sciences, Govi Verlag Pharmazeutischer Verlag GMBH, DE, vol. 47, No. 11, Nov. 1992, pp. 856-861 (6 Pages).

International Search Report and Written Opinion of the International Searching Authority dated Sep. 8, 2017 for International Application No. PCT/IB2017/000757 (17 Pages).

Puttaiah, R., et al., "Dental Unit Water Line Treatment with Sodium Hypochlorite and Acetic Acid", Michochemical Journal, 1998, pp. 333-340 (8 Pages).

International Search Report and Written Opinion of the International Searching Authority dated May 17, 2018 for International Application No. PCT/IB2017/001728 (17 Pages).

* cited by examiner

Stability results under various conditions

HAND DISINFECTANT

RELATED APPLICATIONS

This application is a continuation-in-part of U.S. patent application Ser. No. 14/618,820, filed Feb. 10, 2015, which is a continuation-in-part of U.S. patent application Ser. No. 13/770,738, filed Feb. 19, 2013, which claims priority to and the benefit of U.S. Provisional application Ser. No. 61/600,344, filed Feb. 17, 2012; and this application is a continuation-in-part of U.S. patent application Ser. No. 14/618,799, filed Feb. 10, 2015, which is a continuation of U.S. patent application Ser. No. 13/770,738, filed Feb. 19, 2013, which claims priority to and the benefit of U.S. Provisional application Ser. No. 61/600,344, filed Feb. 17, 2012, the contents of each of which are incorporated by reference herein in their entirety.

FIELD OF THE INVENTION

The invention generally relates to compositions of hand disinfectant and methods of production and use thereof.

BACKGROUND

Healthcare professionals have a significantly higher risk of developing hand eczema, dermatitis, and other skin problems as compared to the general population. These conditions are not only problematic for healthcare works but also impact patient populations. For example, eczema contributes to the spread of infection in hospitals. More than 90% of people with moderate-to-severe eczema are colonized with *Staphylococcus aureus*. Staph infections can be deadly. In particular, antibiotic-resistant strains such as MRSA (methicillin-resistant *Staphylococcus aureus*) are difficult to control. The prevalence of eczema among healthcare employees is therefore a significant problem.

For people with eczema, washing hands with soap and water can lead to further irritation and prevent healing. That is why many healthcare workers instead rely on hand disinfectants as an alternative or a supplement to hand washing. It is estimated that 40% of all hospital-acquired infections comes from poor hand disinfection, and a primary reason for poor hand disinfection is irritated skin. Hand disinfectants or hand sanitizers are generally gel, foam, or liquid solutions with an active ingredient for killing microorganisms. Most hand disinfectants include alcohol in the form of ethanol or isopropanol.

Alcohol-based hand disinfectants can actually exacerbate the problem for those with eczema by promoting the autoimmune response that causes eczema. When exposed to alcohol, the *Staphylococcus aureus* and other bacteria that survive respond by producing a protective biofilm. Biofilms are known to impair cutaneous wound healing and reduce topical antibacterial efficiency, and they can also spread bacteria into the air. Meanwhile, antibiotic resistant bacteria such as MRSA proliferate within the biofilm, leading to many serious and deadly hospital infections. Eczema, especially among healthcare providers, remains a major public health concern.

Summary

The present invention provides a skin disinfectant that is effective for, among other things, treating skin with eczema, preventing bacterial proliferation, combating antimicrobial resistance, preventing biofilm formation, and removing biofilm where it already exists. The invention uses hypochlorous acid (HOCl) and acetic acid as a disinfectant rather than alcohol. HOCl has a high oxidative capacity, which makes it an ideal disinfectant. However, HOCl is also an unstable compound. That limitation has made prior art HOCl-based disinfectants inadequate.

To present invention provides highly-effective but stable HOCl and acetic acid compositions. Hypochlorous acid compositions of the invention are substantially free of metal ions. Compositions of the invention have a balanced pH within a range of about 3.7 to 5.8. The disclosed compositions provide a stable HOCl based skin disinfectant with a long shelf-life, previously unavailable in the art. Other additives and excipients may be included in the composition, which further enhance stability. It should be understood that not all common off-the-shelf additives are compatible because they may degrade the active compound to such an extent that the product loses its activity. Some excipients for use with the formulation are disclosed below.

In certain aspects, the invention provides a composition that includes hypochlorous acid (HOCl), acetic acid (HAc), water; and an excipient. The pH of the composition is between about 3.7 and about 5.8, and preferably about 4.76. The pH is achieved by titrating the composition with NaOH and HAc. The composition is typically produced by mixing in an air-free environment, such as an environment made by degassing through reduced pressure.

The water component of the composition preferably is purified water. The excipient may include a thickening agent and/or a chelator. Excipients may include, for example, inorganic thickeners such as colloidal silica, synthetic clay materials, or the product sold under the trademark LAPONITE by BYK Additives (Cheshire, UK). Excipients may additionally or alternatively include EDTA, polyethylene glycol, polysorbate, glycerol, acrylate copolymer, essential oils, buffers, cellulose derivatives, or xanthan gum.

In certain embodiments, the composition is useful as a hand disinfectant. The composition is useful to treat eczema or an infection, including a *Staphylococcus aureus* infection.

In related aspects, the invention provides a method for disinfecting skin. The method includes providing a composition of hypochlorous acid (HOCl), acetic acid (HAc), water, and an excipient, and applying the composition to skin. In some embodiments, the method also includes breaking down a biofilm on the skin. The biofilm may be associated with a skin infection or eczema. The biofilm may be a *Staphylococcus aureus* biofilm.

In embodiments of methods of the invention, compositions have a pH of between about 3.7 and about 5.8, and preferably about 4.76. The method may further involve titrating the composition with NaCl and HAc. The composition may be produced by mixing in an air-free environment, such as an environment made by degassing through reduced pressure.

The water component of the composition can be purified water. The excipient may include a thickening agent and/or a chelator. Excipients may include, for example, inorganic thickeners such as colloidal silica, synthetic clay materials, or the product sold under the trademark LAPONITE by BYK Additives (Cheshire, UK). Excipients may additionally or alternatively include EDTA, polyethylene glycol, polysorbate, glycerol, acrylate copolymer, essential oils, buffers, cellulose derivatives, or xanthan gum.

DETAILED DESCRIPTION

The present invention recognizes the disinfecting power of HOCl and harnesses it in a stable formulation that is ideal for disinfecting skin. Hypochlorous acid is a reactive species due to its oxidative capacity. In aqueous solution, HOCl is involved in chemical equilibria with other reactants and products. The multiple equilibria can be complex, and in order to control or kinetically delay the breakdown of HOCl, the invention controls several factors in the formulation process. Unlike prior art methods, the present invention stabilizes the HOCl solution by regulating pH, removing metal ions, and reducing ionic strength. Those factors are controlled using a process that combines ion exchange and mixing in a substantially or completely air-free environment such as an air-free environment made by degassing through reduced pressure. The resulting composition retains the reactive advantages of hypochlorous acid but has increased stability, which makes it useful for both the consumer and healthcare provider markets. The storage containers throughout the process (including the final packaging) are configured to be air-free as well as control other variables, such as UV exposure. Protective packaging can help to further stabilize the formulation.

Hypochlorous Acid Production

Compositions and methods of the invention take advantage of the protonation of the hypochlorite ion ($OCl^-$). Using HCl and NaOCl as an example, the protonation is accomplished by introducing an acid (e.g., HCl) to the solution, which results in the following reaction:

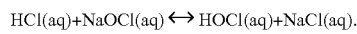

The hypochlorous acid in aqueous solution partially dissociates into the anion hypochlorite ($OCl^-$). Thus in aqueous solution there is always an equilibrium between the hypochlorous acid and the anion ($OCl^-$). That equilibrium is pH dependent and at higher pH the anion dominates. In aqueous solution, hypochlorous acid, is also in equilibrium with other chlorine species, in particular chlorine gas, $Cl_2$, and various chlorine oxides. At acidic pH, chlorine gases become increasingly dominant while at neutral pH the solution is dominated by hypochlorous acid. Thus, it is preferable to control exposure to air and pH in the production of hypochlorous acid.

Any compound that produces a hypochlorite anion ($OCl^-$) in water may be used with methods of the invention. Exemplary compounds include NaOCl and $Ca(OCl)_2$. In particular embodiments, the compound is NaOCl. Any compound that produces a proton ($H^+$) in water may be used with methods of the invention. Exemplary compounds are acids, such as acetic acid, HCl and $H_2SO_4$. In particular embodiments, the compound is HCl. In preferred embodiments, the compound is acetic acid. Acetic acid is a weaker acid than HCl with a preferred pKa. It is more able to maintain the preferred pH level.

Figure 1:
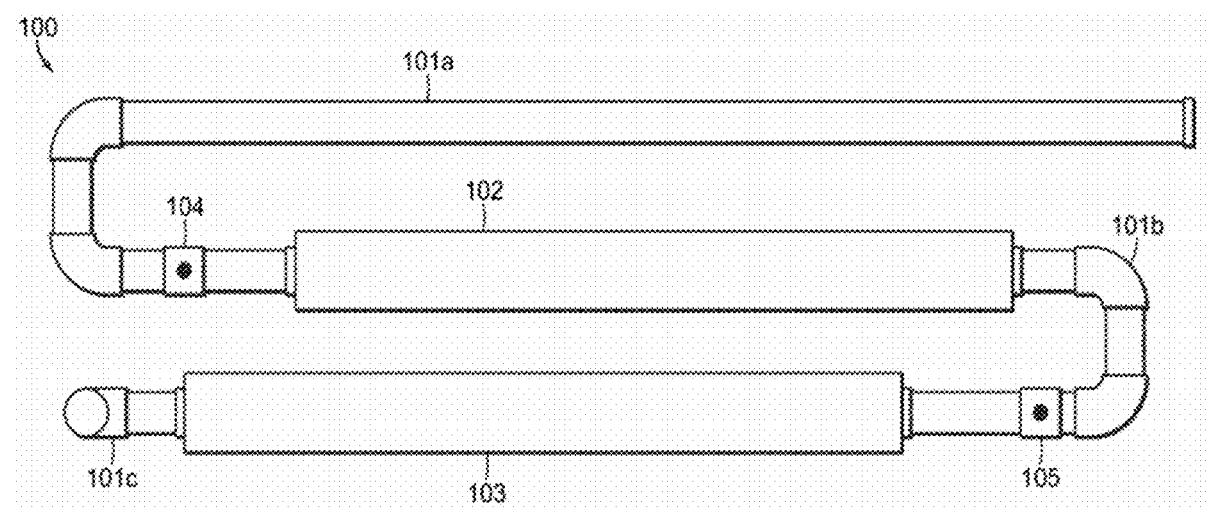
FIG. 1 shows a fluidic system for use with the present invention.

Mixing the compounds can be conducted in a chamber or fluidic system. In certain embodiments, a fluidic system 100 as shown in FIG. 1 is used to perform methods of the invention. The system 100 includes a series of interconnected pipes 101a-c with a plurality of mixing devices 102 and 103 in-line with the plurality of pipes 101a-c. The pipes and the mixing devices can be interconnected using seals such that all air can be purged from the system, allowing for methods of the invention to be performed in an air-free environment. In certain embodiments, methods of the invention are also conducted under pressure. Conducting methods of the invention in an air-free environment and under pressure allows for the production of HOCl that does not interact with gases in the air (e.g., oxygen and $CO_2$) that may destabilize the produced HOCl.

The pipes and mixers can be made from any inert material such that material from the pipes and mixers does not become involved with the reaction occurring within the fluidic system. Exemplary materials include PVC-U. Pipes are commercially available from Georg Ficher AB. The pipes and mixers can be configured to have a linear arrangement such that the pipes and the mixers are arranged in a straight line. Alternatively, the pipes and mixers can have a non-linear arrangement, such that the water must flow through bends and curves throughout the process. System 100 shows a non-linear configuration of the pipes 101a-c and mixers 102 and 103.

Pipe 101a is an inlet pipe that receives the water that will flow through the system. Generally, the water in pipes 101a-c is maintained at a pressure of at least about 0.1 bar, such as for example, 0.2 bar or greater, 0.3 bar or greater, 0.4 bar or greater, 0.5 bar or greater, 0.7 bar or greater, 0.9 bar or greater, 1.0 bar or greater, 1.2 bar or greater, 1.3 bar or greater, or 1.5 bar or greater. At such pressures, a turbulent water flow is produced, thus the reagents are introduced to a highly turbulent water flow which facilitates an initial mixing of the reagents with the water prior to further mixing in the mixing devices 102 and 103.

In certain embodiments tap water is used. In other embodiments, deionized water with the addition of known buffering agents is used. One example of a buffer is phosphate buffer. For greater process control and consistency, using formulated deionized water may be preferable to using tap water because tap water can change between locations and also over time. Additionally, using deionized water with known additives also ensures a stable pH of the incoming water flow.

To introduce the reagents to the water, pipe 101a includes an injection port 104 and pipe 101b includes an injection port 105. The injection ports 104 and 105 allow for the introduction of reagents to the water flow. In this embodiment, aqueous compound that generates the proton is introduced to the water in pipe 101a via injection port 104. The compound that generates the proton is introduced by an infusion pump that is sealably connected to port 104. In this manner, the flow rate, and thus the amount, of compound that generates the proton introduced to the water at any given time is controlled. The infusion pump can be controlled automatically or manually. The rate of introduction of the compound that generates the proton to the water is based upon the incoming water quality (conductivity and pH level) and the pressure and the flow of the incoming water. In certain embodiments, the pump is configured to introduce about 6.5 liters per hour of hydrochloric acid into the water. The introducing can be a continuous infusion or in an intermittent manner. Since the water is flowing though the pipes in a turbulent manner, there is an initial mixing of the compound that generates the proton with the water upon introduction of the hydrochloric acid to the water.

Figure 2:
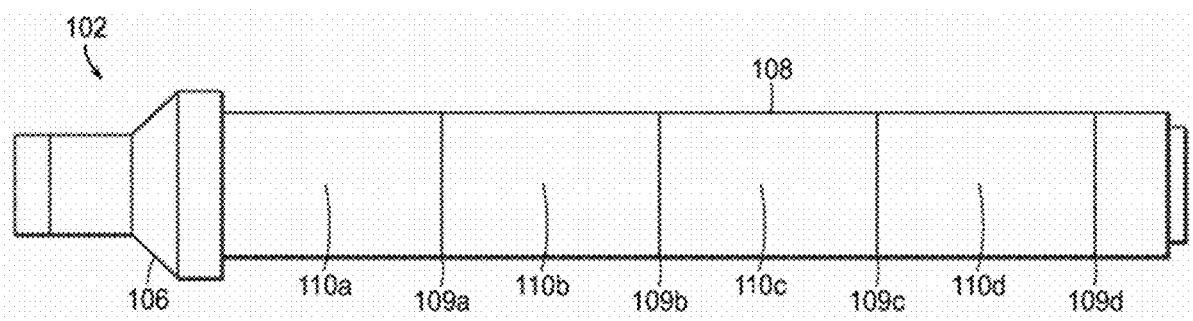
FIG. 2 shows a mixing device for use with the present invention.
Figure 3:
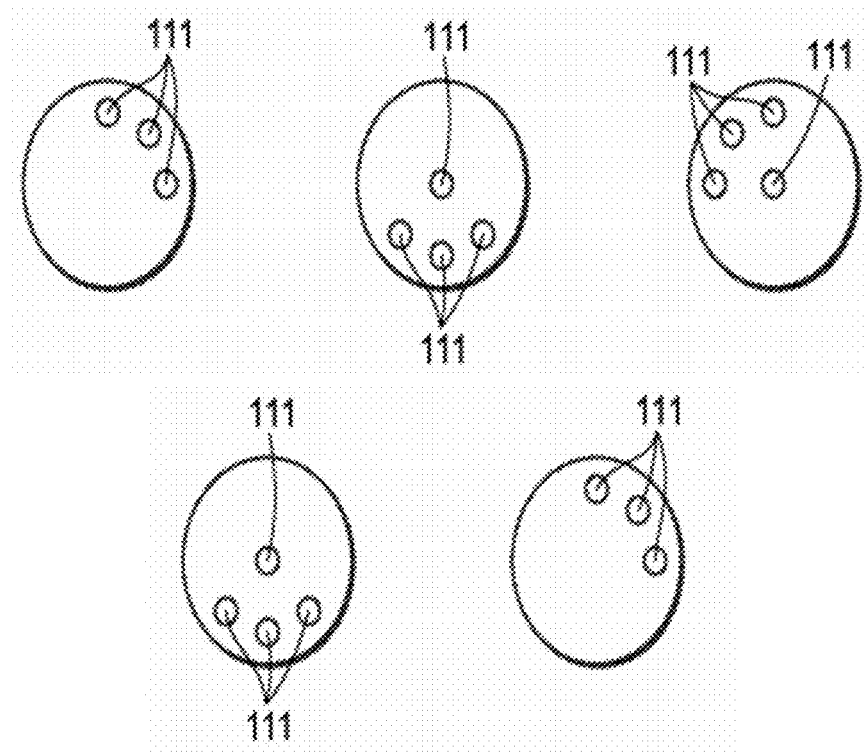
FIG. 3 shows components of the mixing device of FIG. 2.

The mixing device 102 is configured to produce a plurality of fluidic vortexes within the device. An exemplary device configured in such a manner is shown in FIG. 2, which is a figure providing an internal view of the chamber 108 of device 102. The chamber 108 includes a plurality of members 109, the members being spaced apart and fixed within the chamber 108 perpendicular to the inlet and the outlet in order to form a plurality of sub-chambers 110. Each member 109 includes at least one aperture 111 that allows fluid to flow there through. FIG. 3 shows a front view of the members 109 so that apertures 111 can be seen. The size of the apertures will depend on the flow of water and the pressure in the system.

Figure 4:
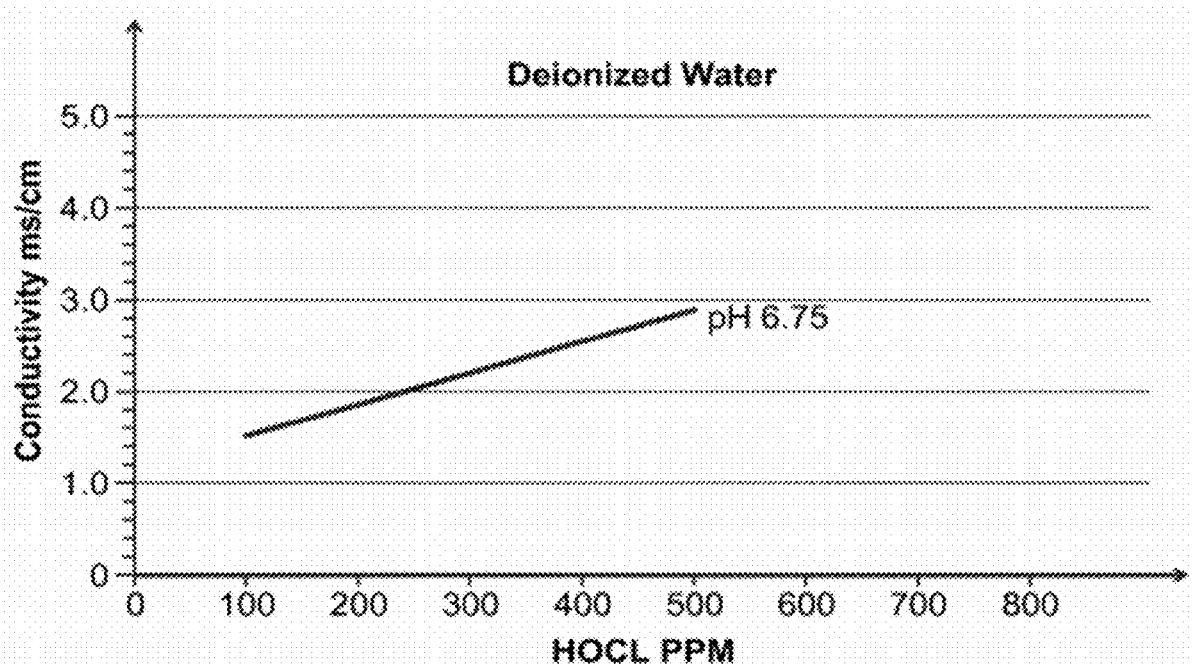
FIG. 4 shows a calibration curve comparing conductivity to HOCl concentration.

The production of HOCl can be controlled in-line by measuring pH and conductivity. The pH is used in combination with conductivity based on a pre-calibrated relation between the conductivity and concentration of HOCl measured with spectrophotometry. The measured conductivity is a measure of the solvent's ability to conduct an electric current. Comparing the same matrix with different known concentrations of HOCl and OCl—, a calibration curve (FIG. 4) has been established that is used in combination with the pH meter to regulate the titrations and control the process.

Figure 5:
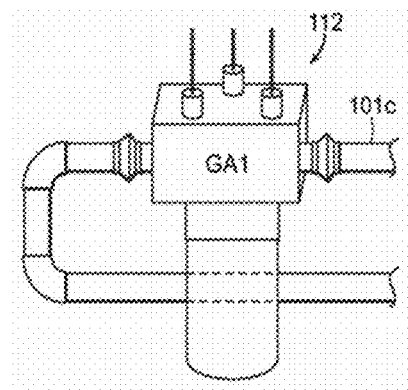
FIGS. 5 and 6 show a switch valve and waste line.
Figure 6:
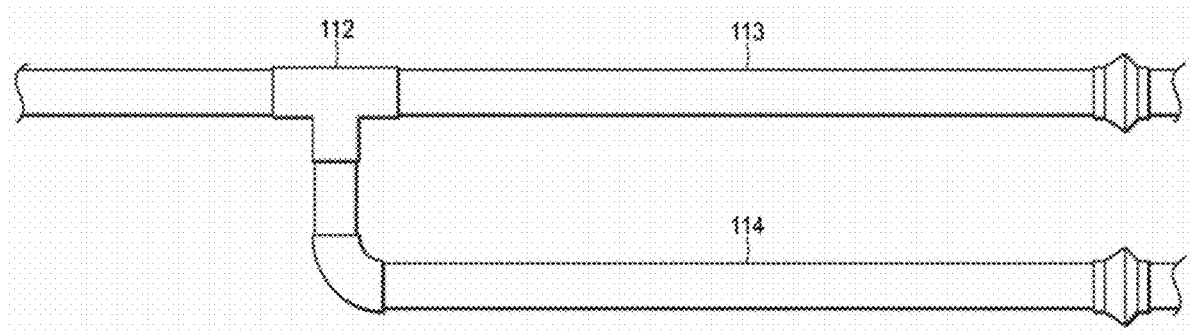

As shown in FIGS. 5 and 6, pipe 101c can be connected to a switch valve 112 that switches between a waste line 113 and a product collection line 114. The valve 112 includes the pH meter and the conductivity measuring device. These devices measure the concentration (ppm), purity, and pH of the HOCl being produced and provide feedback for altering such properties of the produced HOCl. Once the HOCl being produced in pipe 101c meets the required concentration, purity, and pH, the valve 112 switches from the waste line 113 to the product collection line 114 to collect the desired product.

The HOCl that has been produced in an air-free manner is collected and bottled in an air-free manner. Placing liquids into a bottle in an air-free manner is known in the art. An exemplary method includes placing an inflatable vessel (such as a balloon) into a bottle. The inflatable vessel is connected directly to the collection line 114 and the HOCl is pumped directed into the inflatable vessel in the bottle without ever being exposed to air. Another method involves filling the bottles under vacuum. Another air-free filling method involves filling the bottles in an environment of an inert gas that does not interact with the HOCl, such as an argon or nitrogen environment.

The produced hypochlorous acid is air-free and will have a pH from about 4.5 to about 7.5. However, the pH of the produced HOCl can be adjusted post production process by adding either acid (e.g., HAc) or alkali (e.g., NaOH) to the produced hypochlorous acid. For example, a pH of between about 4.5 and about 7 is particularly suitable for the application of reprocessing heat sensitive medical instruments. Other applications, such as its use in non-medical environments, for example as in the processing of poultry and fish and general agricultural and petrochemical uses, the breaking down of bacterial biofilm and water treatment, may demand different pH levels.

Product Stability

The invention controls several factors that contribute to the stability of the final product. Those factors include air exposure, pH, buffering capacity, ion concentration, the presence of metal ions, and packaging that blocks UV light exposure. As will be evident from the following discussion, those factors are interrelated in a variety of ways.

Protecting the composition from exposure to air contributes to HOCl stability. Methods and devices for producing HOCl in an air-free environment are described in US 2013/0216628 and US 2013/0215709, both of which are hereby incorporated by reference in their entirety. One reason that producing HOCl and mixing the hand disinfectant composition in an air-free environment, such as an environment degassed through reduced pressure, helps stability is that it reduces or avoids the presence of carbon dioxide ($CO_2$), which is present in air. $CO_2$ dissolves readily in water (approximately 1.5 g/L). Furthermore, the equilibrium between air and water is established within minutes. When dissolved $CO_2$ reacts with water, it forms $H_2CO_3$, which is an acid. $H_2CO_3$ deprotonates in water, releasing $H_3O^+$, which decreases the pH of the water.

$CO_2$ can be removed from a water solution by heating or by purging the water with $N_{2(g)}$. Purging replaces the $CO_2$ with $N_2$. But that does not fully solve the problem if the solution is still exposed to air. Since the solubility of $CO_2$ in water is high, new $CO_2$ will quickly be re-dissolved and replace the $N_2$ unless the water is protected from interactions with air.

In addition to $CO_2$, oxygen is another reactive molecule present in air that dissolves in water, although not as fast and not to the same degree as $CO_2$. Like $CO_2$, oxygen can be removed from a water solution by heating or by purging $N_{2(g)}$ through the water to replace $O_2$ with $N_2$. In a solution of HOCl, $O_2$ can react with the hypochlorous ion $ClO^-$ and form the chlorate ion $ClO_3^-$. That reaction is pH dependent, which is one reason that pH control is an important factor. The reaction does not proceed to an appreciable extent at lower pH, such as approximately 4.0.

There are additional reasons why the present invention seeks to control pH. Several of the equilibria involved in a mixture of HOCl in water are pH dependent, which means that controlling the pH is extremely important. The pH must be controlled at all stages: during production of the HOCl; during production of the hand disinfectant formulation; and during storage of the formulation product.

HOCl in water is in equilibrium with the less potent $OCl^-$ ion. At higher (more basic) pH, the $OCl^-$ ion dominates. Therefore, lower pH, where the more potent HOCl dominates yields a superior product. At a pH around 4.0 to 5.0, there will not be much production of $Cl_{2(g)}$.

To achieve that optimal pH, the invention uses NaOH and acetic acid to titrate the water to the right pH. The choice of acetic acid is important because it has a pKa of 4.76, and so its maximum buffering capacity is at pH 4.76. Acetic acid is therefore a good choice for titrating the solution to create a product that is dominated by HOCl rather than $OCl^-$.

Ionic strength is another important factor in the stability of HOCl. Ionic strength is correlated with the total concentration of ions in the solution. For HOCl, it has been shown that higher ionic strength, which can result from the use of buffers that add ions to the solution, actually destabilizes the HOCl (see Adam et al., Inorg. Chem. 1992, 31, 3534-41). Thus not all buffers increase the stability of the HOCl. Starting with an optimum pH and using an acid with the right pKa (such as acetic acid, as described above) prevents the need to titrate with a surplus of ions. The combination of NaOH and HAc to make a HAc-NaAc buffer has been found to provide better stability than using NaOH and HCl. The combination of NaOH and HCl increases ionic strength and also increases chloride ions, which hurt stability as well. It is also better than a phosphate buffer system that was found to have worse stability.

In certain embodiments, the incoming water has a pH of 6 before titration. If the water has been in contact with air such that $CO_2$ has dissolved, the pH can be lower than 6. In that case, more NaOH is added, leading to a higher total number of ions in the solution, which destabilizes the product.

Various factors go into which buffer to choose. A buffer can stabilize the pH (which has a positive effect on product stability) and at the same time increase the ionic strength (which has a negative effect). Different buffers will not have the same positive effect (depending on their pKa), or the same negative effect (mono-, di-, and trivalent ions have different impact on ionic strength).

Another stability factor that the invention controls is the presence of metal ions in the solution. Metal ions such as $Fe^{2+}$, $Fe^{3+}$, and $Mn^{2+}$ are a source of destabilization. Metal ions are not removed by purging with $N_2$ or heating the water. In the pharmaceutical industry, EDTA is used in order to capture or chelate the metal ions. That ensures that they do not initiate a catalytic breakdown. However, adding EDTA to the solution is not desirable for HOCl because the EDTA would be oxidized, resulting in production of toxic chlorine gas, $Cl_{2(g)}$. The metal ions are present in their charged ionic form, and so the invention uses an ion exchange method to remove them.

The ion exchange removes metal ions and $CO_2$ (through the removal of $CO_3^{2-}$ and $HCO_3^-$ ions) and assures a near neutral pH of the incoming water. That approach reduces the ionic strength of the final product. Protecting the composition from air by mixing in an air-free environment helps to further stabilize pH since it protects the water from $CO^2$. The water can be run through the ion exchange mass twice, which helps to remove $CO_3^{2-}$ and $HCO_3^+$ as well as removing more metal ions in order to prevent catalytic reactions.

Prior art methods of only using $N_{2(g)}$ to remove gas such as oxygen and carbon dioxide fail to reduce the number of metal ions and also fail to prevent interaction with air. Additionally, those methods do not assure that the incoming process water has the correct pH to reduce the final ionic strength of the product.

Figure 7:
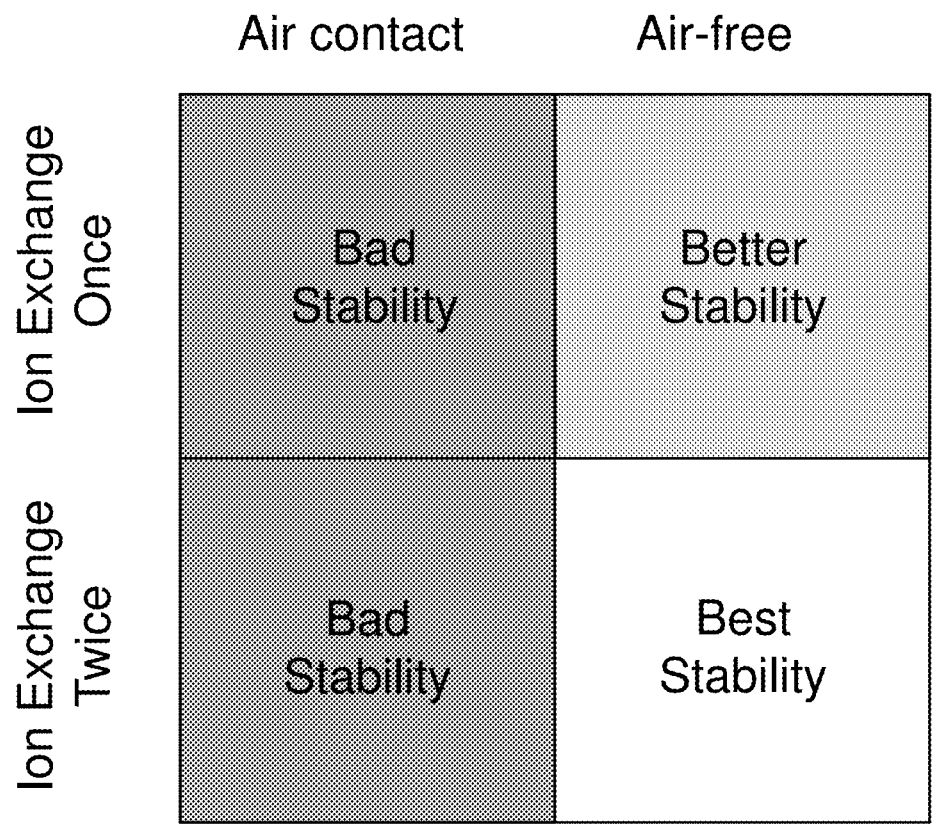
FIG. 7 shows a comparison of stabilities achieved under different conditions.

FIG. 7 shows a comparison of stabilities achieved under different conditions. When HOCl is produced in the presence of air, the result is bad stability, regardless of whether one or two ion exchange cycles were used. As shown in the chart, protecting the solution from air improves stability. The air-tight process in combination with two ion exchange cycles provides a significantly higher stability than only one ion exchange cycle. That result confirms that control of the reactions and equilibria discussed above is an important factor in stability of the composition.

Disinfectant Formulation

The improved stability of HOCl achieved by the present invention makes it much more useful as a disinfectant than previously possible. The disinfectant properties of HOCl are generally known. HOCl is a weak acid that is known to rapidly inactivate bacteria, spores, viruses, algae, fungi, and other organics, making it an effective agent for across a broad range of microorganisms. Humans produce certain compounds such as taurine that allow them to tolerate hypochlorous acid, and so it is a safe disinfectant for use on skin. But HOCl produced by traditional methods is highly unstable, and over a short period of time (e.g., a few hours to a couple of weeks) the hypochlorous acid degrades. Thus, while being an effective biocide, the use of hypochlorous acid has previously been limited by the need for onsite generation and the challenge of maintaining storage stability.

Compositions and methods of the present invention, however, provide a stable HOCl-based hand disinfectant. A preferred embodiment of the formulation includes HOCl, acetic acid (HAc), water, and an excipient. The formulation can be titrated with NaOH and HAc to obtain a pH of about 4.6-4.7.

In addition to buffering the product during storage and after application, acetic acid also has the advantage of improving the sporicidal effect by 40% compared to other acids used for protonization of HOCl.

As discussed above, pH is an important factor that is controlled throughout the production process of the invention. When pH is too low, chlorine gas will evolve which is undesirable. When pH is too high (like most other HOCl products on the market) then the product equilibrium is dominated by the less-potent $OCl^-$ ions. Formulations of the present invention can have a pH in the range of 3.0 to 8.0, although formulations at the higher end of that range will be much less potent than a formulation at the preferred pH of between 4.0 and 5.0, and even more preferably 4.76. Acetic acid has a buffering capacity between approximately 3.7 and 5.8.

The formulation of the present invention includes an additive or excipient. Excipients provide different qualities to the final product, such as a desired viscosity for pumping and handling. Excipients may include a thickening agent and/or a chelator. Excipients may include, for example, inorganic thickeners such as colloidal silica, synthetic clay materials, or the product sold under the trademark LAPONITE by BYK Additives (Cheshire, UK). Excipients may additionally or alternatively include EDTA, polyethylene glycol, polysorbate, glycerol, acrylate copolymer, essential oils, buffers, cellulose derivatives, or xanthan gum Additives can also be added for a hydrating effect, which is desirable for topical products. Additives can also be added for improving fragrance, cleansing, preservation, or to impart other qualities on the final product, which may take the form of a cream, gel, lotion, balm, or other topical ointment.

Below many additives are discussed that are commonly used in hand disinfectant products known in the art. Because HOCl is an oxidative species the choice of additive is not trivial. Some additives should not be used with HOCl at the preferred pH levels. The list of additives discussed below includes common excipients used in hand disinfectant products or other similar product types, and is a non-comprehensive list of additives for use with the invention.

Some of the excipients discussed are more desirable than others, based partly on their susceptibility to oxidation, which affects shelf-life. Even less desirable excipients can still be used, partly depending on other factors such as molecular variability (cross-linkers in certain polymers, for example), the presence of metal ions (glycerol in particular), and chemical origin (polyethylene glycol-based surfactants or sugar-based surfactants, for example).

With any of the excipients, oxidation will occur, but some will provide a longer time horizon. Even the excipients discussed below that have a relatively short time horizon would still provide usable shelf-life for the product, particularly because HOCl in this formulation is in a very low concentration.

One excipient commonly used with topical formulations is ethylenediaminetetraacetic acid (EDTA). EDTA is the chelating agent commonly used to diminish the catalytic reactivity of trace metal ions in purified water. In the presence of HOCl, EDTA will be oxidized to glyoxylic acid and formaldehyde, and the HOCl will be reduced to chlorine gas. The latter is known to happen when EDTA is added to a concentrated solution of HOCl/OCl⁻. The kinetics will be slower at the relatively low concentrations of HOCl in the preferred formulation of the invention, but nevertheless it is a degrading combination. Thus, other excipients may be preferable to EDTA. In preferred embodiments of the invention, metal ions are removed through the proprietary ion exchange process rather than by using EDTA.

Polyethylene glycol (PEG) is another common excipient. However, PEG is very sensitive to oxidation and will be degraded by HOCl, resulting in oxidation products such as aldehydes, ketones, acids and dioxolanes, as well as a strong odor and pH destabilization.

Another excipient frequently found in hand disinfectants is any of a number of common essential oils. These will be degraded through oxidation (see, e.g., Turek & Stintzing, 2014, "Stability of Essential Oils: A Review," Comprehensive Reviews in Food Science and Food Safety). The result may be degradation products that lead to bad odors and pH destabilization, like with PEG.

Buffers are also potential excipients. As discussed above, many buffer systems increase the ionic strength of the solution, creating a destabilizing effect. A buffer system of NaOH and acetic acid is preferred by the invention.

Polysorbates (Polysorbate 20 and Polysorbate 80) are also common additives, but those too are prone to oxidative degradation (see Borisov et al. "Oxidative Degradation of Polysorbate Surfactants Studied by Liquid Chromatography—Mass Spectrometry" J. Pharm. Sci. 194(3), 2015).

Polymers, such as any type of acrylate copolymer, which are well known to those of skill in the art, can function well in the formulation of the invention. Acrylate copolymers are homo- and co-polymers of acrylic acid cross-linked with a polyalkenyl polyether. Acrylate copolymers come with a variety in graft density. They vary in terms of their ability to oxidize and how many grafted chains there are per polymer. One possible cross-linker is pentaerytritol which is very stable, and so it is a good choice for use with the present invention. Polyacrylic acid (PAA) polymers that are known to stabilize formulations of $H_2O_2$ can be used with the present invention. (see Schmucker-Castner & Desai, 1999, "Rheology Modification of Hydrogen Peroxide Based Applications Using A Cross-linked PAA polymer," Int J Cosmet Sci 21(5):313-25).

Many other excipients may be used. Inorganic thickeners such as silica and laponite (a synthetic clay material related to silica) may provide better results. For example, silica works well to create a gel and to retain the concentrations of HOCl. Glycerol, or glycerin, is another common excipient. It can also be oxidized, but in the absence of metal ions or a metal surface, that will not cause a problem for the product shelf-life. Cellulose derivatives are other common excipients. One example is hydroxyl-propyl cellulose. Another embodiment uses xanthan gum, which is a nature-derived, high-molecular weight polysaccharide often used in skin product formulations to achieve the desired rheological characteristics. Colloidal silica as a viscosity modifier can be used at the lower pH if the silica is cationically modified. Sugar-based surfactants and other surfactants are known in the art as well.

Formulation Process

The process for making the final product formulation involves purifying water, adding excipients, adding NaOCl and HAc reactants, and filling the formulation into air-free packaging to sustain its shelf-life. The entire process is performed under air-free environmental conditions.

Water, such as regular drinking water or deionized water, is provided. The water can be run through a purifying process one or more times, to remove organisms and ions. An excipient in liquid or powder form can be mixed together with the purified water in an air-free environment. The air-free environment can be made by degassing through reduced pressure. The excipient may be a product thickener or it may be any other excipient described herein, which can be added to achieve different viscosity, fragrance, or other properties.

The formulation may be titrated with, for example, NaOH and HAc, to a final pH of between 4.0 and 5.0, preferably about 4.76. The finished hand disinfectant is filled into an air free container such as an air-tight bag, for later filling in consumer air-free packaging, as is known in the art.

It should be noted that in addition to the process parameters for generating the air-free HOCl solution and final product, the various storage containers throughout the process (including the final packaging) are configured to control other variables as well, such as UV exposure. Protective packaging can further slow the breakdown process.

The production process can be manual or automated with a computer. Fluidic systems described herein can be operably connected to a computer that controls the production process. The computer may be a PCL-logic controller system. The computer opens and closes valves for the water inlet, the waste water outlet, and the product outlet according to the feedback received from the sensors in the system (e.g., conductivity, pH, and concentration of product (ppm) being produced). The computer can also store the values for the water pressures and water amounts and can adjust these according to the feedback received from the sensors regarding the properties of the product being produced. The computer can also control the infusion pumps that inject the reagents into the water for the production process.

Incorporation by Reference

Any and all references and citations to other documents, such as patents, patent applications, patent publications, journals, books, papers, and web contents, which have been made throughout this disclosure, are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. An air-free composition comprising:
   hypochlorous acid (HOCl);
   acetic acid (HAc) at a higher concentration than the HOCl;
   water; and
   an excipient comprising a thickening agent;
   wherein the composition is made air-free by mixing in an air-free environment made air-free by degassing through reduced pressure and the HOCl and HAc are in concentrations that are not harmful to skin.

2. The composition of claim 1, wherein the composition comprises a pH between 3.7 and 5.8.

3. The composition of claim 2, wherein the composition comprises a pH of 4.76.

4. The composition of claim 3, wherein the composition is titrated with NaOH and HAc.

5. The composition of claim 1, wherein the water comprises purified water.

6. The composition of claim 1, wherein the excipient comprises a substance selected from the group consisting of colloidal silica, synthetic clay materials, EDTA, polyethylene glycol, polysorbate, glycerol, acrylate copolymer, essential oils, buffers, cellulose derivatives, and xanthan gum.

7. The composition of claim 1 for use as a hand disinfectant.

8. A method for disinfecting skin, the method comprising applying to skin an air-free composition produced by mixing in an air-free environment made by degassing through reduced pressure, the composition comprising hypochlorous acid (HOCl), acetic acid (HAc) at a higher concentration than the HOCl, water, and an excipient; wherein the HOCl and HAc are in concentrations that are not harmful to skin.

9. The method of claim 8, wherein the skin is broken or inflamed.

10. The method of claim 8, further comprising breaking down a biofilm on the skin.

11. The method of claim 10, wherein the biofilm is associated with a skin infection.

12. The method of claim 10, wherein the biofilm is associated with eczema.

13. The method of claim 10, wherein the biofilm is a *Staphylococcus aureus* biofilm.

14. The method of claim 8, wherein the composition comprises a pH between 3.7 and 5.8.

15. The method of claim 14, wherein the composition comprises a pH of 4.76.

16. The method of claim 15, wherein the composition is titrated with NaOH and HAc.

17. The method of claim 8, wherein the water comprises purified water.

18. The method of claim 8, wherein the excipient comprises a thickening agent.

19. The method of claim 8, wherein the excipient comprises a substance selected from the group consisting of colloidal silica, synthetic clay materials, EDTA, polyethylene glycol, polysorbate, glycerol, acrylate copolymer, essential oils, buffers, cellulose derivatives, and xanthan gum.

* * * * *